United States Patent
Gagner et al.

(10) Patent No.: US 9,549,737 B2
(45) Date of Patent: *Jan. 24, 2017

(54) METHODS AND DEVICES FOR PERFORMING GASTROPLASTY

(71) Applicant: Michel Gagner, Montréal (CA)

(72) Inventors: Michel Gagner, Montréal (CA); David J. Blaeser, Brooklyn Park, MN (US); Dale J. Spencer, Wayzata, MN (US)

(73) Assignee: Michel Gagner, Montréal (CA)

( * ) Notice: Subject to any disclaimer, the term of this patent is extended or adjusted under 35 U.S.C. 154(b) by 213 days.

This patent is subject to a terminal disclaimer.

(21) Appl. No.: 14/174,802

(22) Filed: Feb. 6, 2014

(65) Prior Publication Data
US 2014/0155918 A1 Jun. 5, 2014

Related U.S. Application Data

(63) Continuation of application No. 12/865,709, filed as application No. PCT/US2009/032741 on Jan. 30, 2009, now Pat. No. 8,663,149.

(60) Provisional application No. 61/025,619, filed on Feb. 1, 2008.

(51) Int. Cl.
| *A61B 17/00* | (2006.01) |
| *A61B 17/115* | (2006.01) |
| *A61B 17/072* | (2006.01) |
| *A61F 5/00* | (2006.01) |

(52) U.S. Cl.
CPC ....... *A61B 17/115* (2013.01); *A61B 17/07207* (2013.01); *A61F 5/0083* (2013.01); *A61B 2017/00278* (2013.01); *A61B 2017/00818* (2013.01); *A61B 2017/00827* (2013.01)

(58) Field of Classification Search
CPC ............. A61B 17/115; A61B 17/07207; A61B 2017/00278; A61B 2017/00818; A61B 2017/00827; A61F 5/0083
See application file for complete search history.

(56) References Cited

U.S. PATENT DOCUMENTS

| 5,718,666 A | 2/1998 | Alarcon |
| 6,773,441 B1 | 8/2004 | Laufer et al. |
| 8,663,149 B2 * | 3/2014 | Gagner et al. ................... 604/8 |
| 2003/0220657 A1 | 11/2003 | Adams |
| 2005/0251158 A1 | 11/2005 | Saadat et al. |
| 2007/0167960 A1 | 7/2007 | Roth et al. |
| 2011/0213390 A1 | 9/2011 | Kraemer et al. |

FOREIGN PATENT DOCUMENTS

WO   WO2006/023764 A2   3/2006

OTHER PUBLICATIONS

WIPO, U.S. International Search Authority, International Search Report and Written Opinion mailed Mar. 12, 2009 in International Patent Application No. PCT/US2009/032741, 8 pages.

(Continued)

*Primary Examiner* — Tatyana Zalukaeva
*Assistant Examiner* — Benjamin Klein
(74) *Attorney, Agent, or Firm* — Inskeep IP Group, Inc.

(57) ABSTRACT

A gastroplasty method involves a staple line that terminates prior to reaching the gastroesophageal junction such that the bypassed portion of the stomach does not require resection. Additionally, bougies are taught that assist a physician in following the improved staple line of the present invention.

12 Claims, 7 Drawing Sheets

(56) References Cited

OTHER PUBLICATIONS

United States Patent and Trademark Office, Notice of Allowance mailed Oct. 11, 2013 in U.S. Appl. No. 12/865,709, 12 pages.
United States Patent and Trademark Office, Office Action mailed Jul. 2, 2013 in U.S. Appl. No. 12/865,709, 10 pages.
IP Australia, Examination Report dated Apr. 26, 2013 in Australian Patent Application No. 2009-208954, 3 pages.
United States Patent and Trademark Office, Final Office Action mailed Feb. 26, 2013 in U.S. Appl. No. 12/865,709, 15 pages.
United States Patent and Trademark Office, Office Action mailed Oct. 9, 2012 in U.S. Appl. No. 12/865,709, 11 pages.

\* cited by examiner

METHODS AND DEVICES FOR PERFORMING GASTROPLASTY

PRIORITY CLAIM TO RELATED APPLICATIONS

This application is a continuation of and claims priority to U.S. patent application Ser. No. 12/865,709, filed Feb. 28, 2011, entitled Methods And Devices For Performing Gastroplasty, which is the U.S. National Phase of and claims priority to International Patent Application No. PCT/US2009/032741, International Filing Date Jan. 30, 2009, entitled Methods And Devices For Performing Gastroplasty, which claims priority to U.S. Provisional Patent Application Ser. No. 61/025,619, filed Feb. 1, 2008 by Gagner et al., entitled Methods And Devices For Performing Gastroplasty, the contents of all of which are incorporated herein in their entireties.

BACKGROUND OF THE INVENTION

The present invention relates generally to improved methods and devices for anchoring a gastroenterologic sleeve within the stomach without reliance on sutures, staples, or other mechanisms that puncture the stomach wall. In addition to leaving the stomach walls free of punctures, the anchoring system of the present invention prevents movement of the sleeve in both directions, thereby preventing the sleeve from being passed through the digestive system but also from refluxing up the esophagus.

According to the Center for Disease Control (CDC), sixty six percent of American are overweight, and thirty two percent are obese, presenting an overwhelming health problem. From an economic standpoint, it is estimated that more than 100 billion dollars are spent on obesity and treating its major co-morbidities. This figure does not include psychological and social costs. Many health care experts consider obesity the largest health problem facing westernized societies and considered obesity an epidemic. From a medical standpoint, obesity is the primary risk factor for type 2 diabetes and obstructive sleep apnea. It increases the chances for heart disease, pulmonary disease, infertility, osteoarthritis, cholecystitis and several major cancers, including breast and colon cancers. Despite these alarming facts, treatment options for obesity remain limited.

Treatment options include dietary modification, very low-calorie liquid diets, pharmaceutical agents, counseling, exercise programs and surgery. Diet and exercise plans often fail because most individuals do not have the discipline to adhere to such plans. When diet and exercise fail, many try dietary supplements and drugs or other ingestible preparations promoted as being capable of suppressing appetite or inducing satiety. In general, these techniques for treating compulsive overeating/obesity have tended to produce only a temporary effect. The individual usually becomes discouraged and/or depressed after the initial rate of weight loss plateaus and further weight loss becomes harder to achieve. The individual then typically reverts to the previous behavior of compulsive overeating.

Surgical procedures that restrict the size of the stomach and/or bypass parts of the intestine are the only remedies that provide lasting weight loss for the majority of morbidly obese individuals. Surgical procedures for morbid obesity are becoming more common based on long-term successful weight loss result.

Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found on the website of the American Society for Bariatric Surgery at http://www.asbs.org, the contents of which are incorporated by reference herein in their entirety.

Advances in laparoscopic surgery have allowed physicians to perform operations that previously required an invasive and painful access incision to be made. For example, in the case of a sleeve gastrectomy, a surgeon would make an abdominal incision, typically 5 cm or more in length, which provided access to the abdominal cavity. The surgeon would then suture the stomach together, forming a stoma, using a bougie as a guide along the lesser curvature of the stomach. A bougie is a relatively simple, solid tube inserted into the stomach via the esophagus. The surgeon sutures the stomach shut around the bougie, such that the stoma formed matches the size and the narrow, tubular shape of the bougie.

Conducting this surgery laparoscopically minimizes trauma to the patient because the large abdominal incision is avoided. In female patients, the vagina may be used as an entry point, further minimizing trauma to the abdomen. Recovery time and the chances for infection are greatly reduced using laparoscopic surgery.

However, laparoscopic surgery adds certain complications. In the case of a sleeve gastrectomy, because the suture line extends along the entire length of the stomach, a majority of the stomach is completely isolated from the digestive path. This stomach portion must be removed from the body. Hence, a sleeve gastrectomy begins with the transection of the short gastric arteries to the left diaphragmatic crus. Care must be taken to avoid damaging the spleen or its vessels. This makes removal of the unused stomach portion the most complicated aspect of a sleeve gastrectomy, whether performed laparoscopically or surgically. Laparoscopically transecting these arteries and removing the unused stomach portion is significantly more difficult than doing so surgically. In the case of a vaginal-entry laparoscopy, removing the resected stomach portion through the entry opening in the vagina can be particularly difficult, especially considering that the typical patient undergoing such a surgery as a significantly enlarged stomach.

There is an apparent need for a device and method of performing a sleeve gastrectomy obviates the need for removing any portion of the stomach. If the entire stomach can be left in place, patient recovery time, procedural complexity, and patient morbidity rates will be greatly reduced.

SUMMARY OF THE INVENTION

The present invention provides a device and method for performing a sleeve gastrectomy while obviating the need to resect the bypassed portion of the stomach. The need for resection is obviated by ending suture line a relatively short distance from the gastroesophageal junction. By leaving this small opening between the stoma and the bypassed portion of the stomach, the bypassed portion can remain in place without complication, despite the absence of food.

To prevent food from passing through this opening, the suture line is angled away from the gastroesophageal junction near the top of the stomach. This is effected by the use of an embodiment of a bougie of the present invention. The bougie includes an extension that, when opened, gives the bougie a Y shape. The resulting stoma has an open top near the gastroesophageal junction but, due to the extension, it is funnel-shaped and thus directs food into the stoma instead of the bypassed stomach. Several embodiments of bougies are described herein.

DETAILED DESCRIPTION OF THE INVENTION

Figure 6:
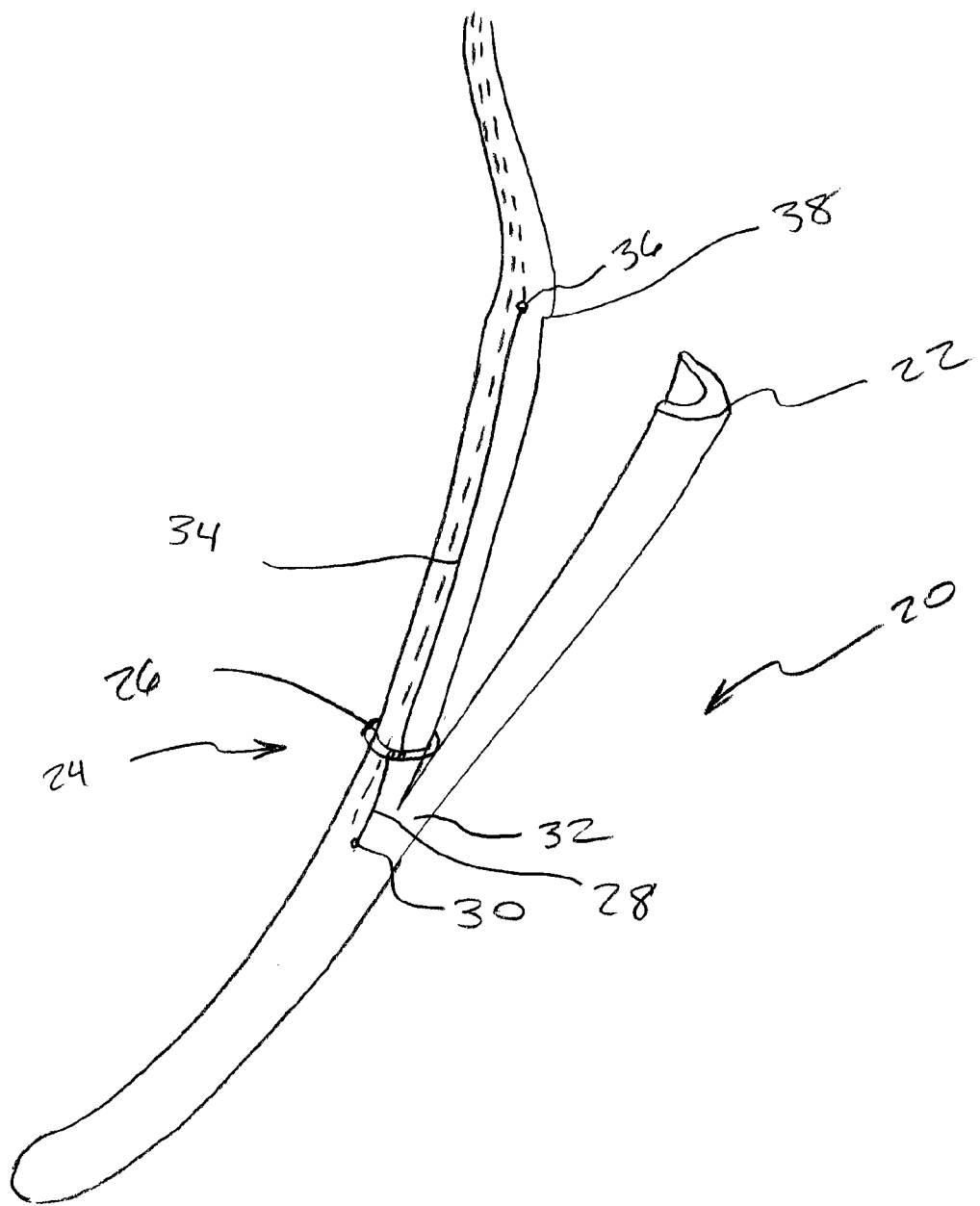
FIG. 6 is a perspective view of an embodiment of a device of the present invention; and, FIG. 7 is a perspective view of an embodiment of a device of the present invention.
Figure 7:
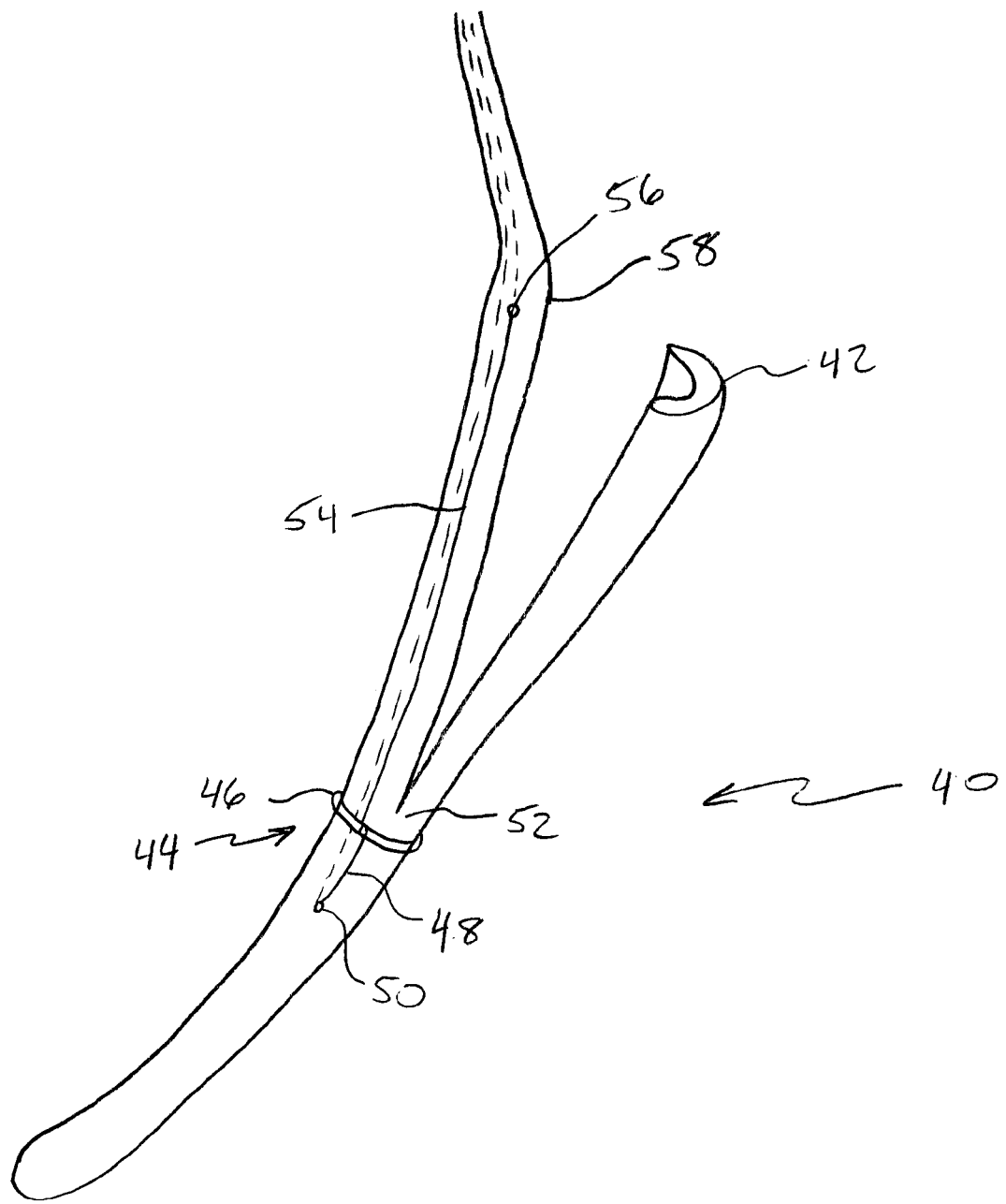

The present invention includes a method and devices for performing a gastroplasty procedure. FIGS. 1-5 show a series of diagrams detailing the various steps of the method. FIGS. 6-7 depict several embodiments of various devices. By explaining the method first, the various embodiments of devices will be more easily understood.

The gastroplasty method of the present invention begins by introducing a bougie 10 into the stomach A via the esophagus B. The bougie 10 is preferably shaped to follow the lesser curve C of the stomach A.

Figure 1:
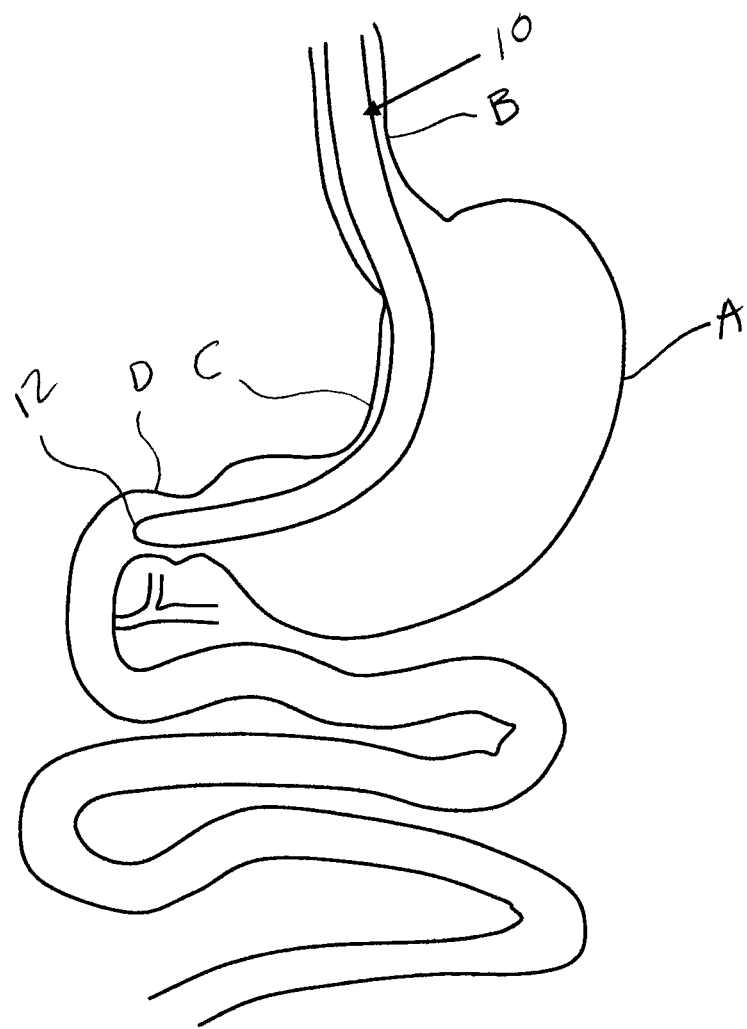
FIG. 1 is an elevation of a first step of the method of the present invention.
Figure 2:
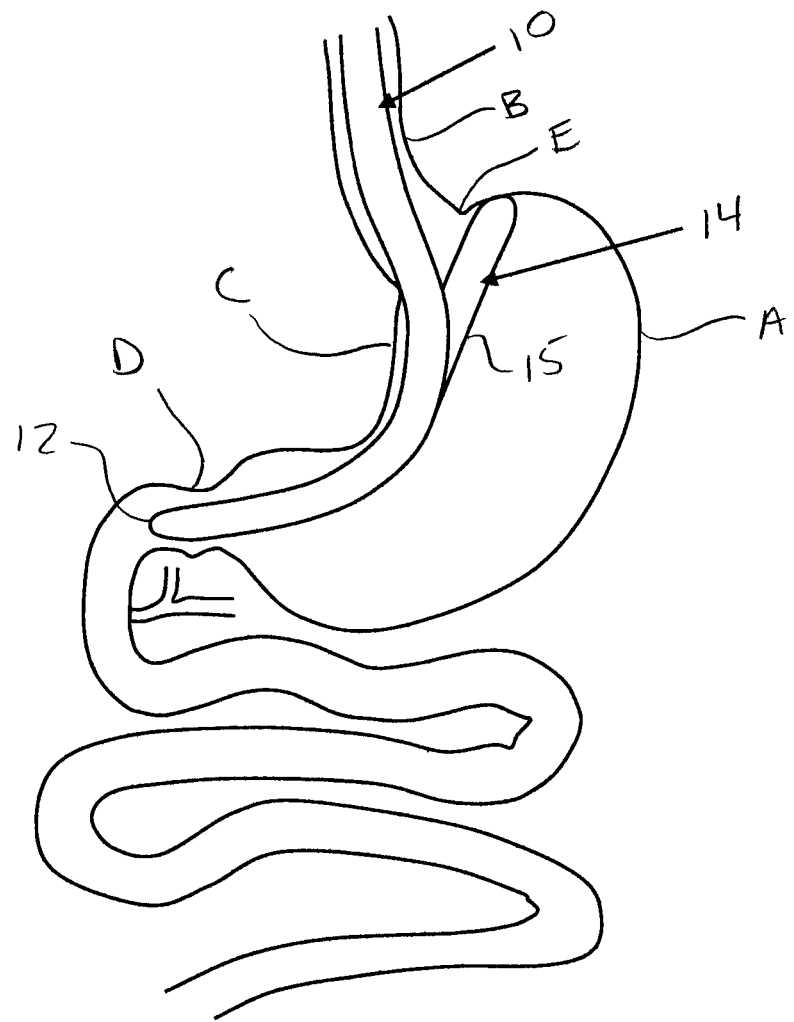
FIG. 2 is an elevation of a second step of the method of the present invention.

Once the bougie 10 is in place such that its distal end 12 is near the gastro-duodenal junction D, an extension 14 of the bougie 10 is splayed open as depicted in FIG. 2. The extension 14 opens enough such that the inner edge 15 of the bougie 10, opposite the lesser curve C, extends away from the gastroesophageal junction E.

Figure 3:
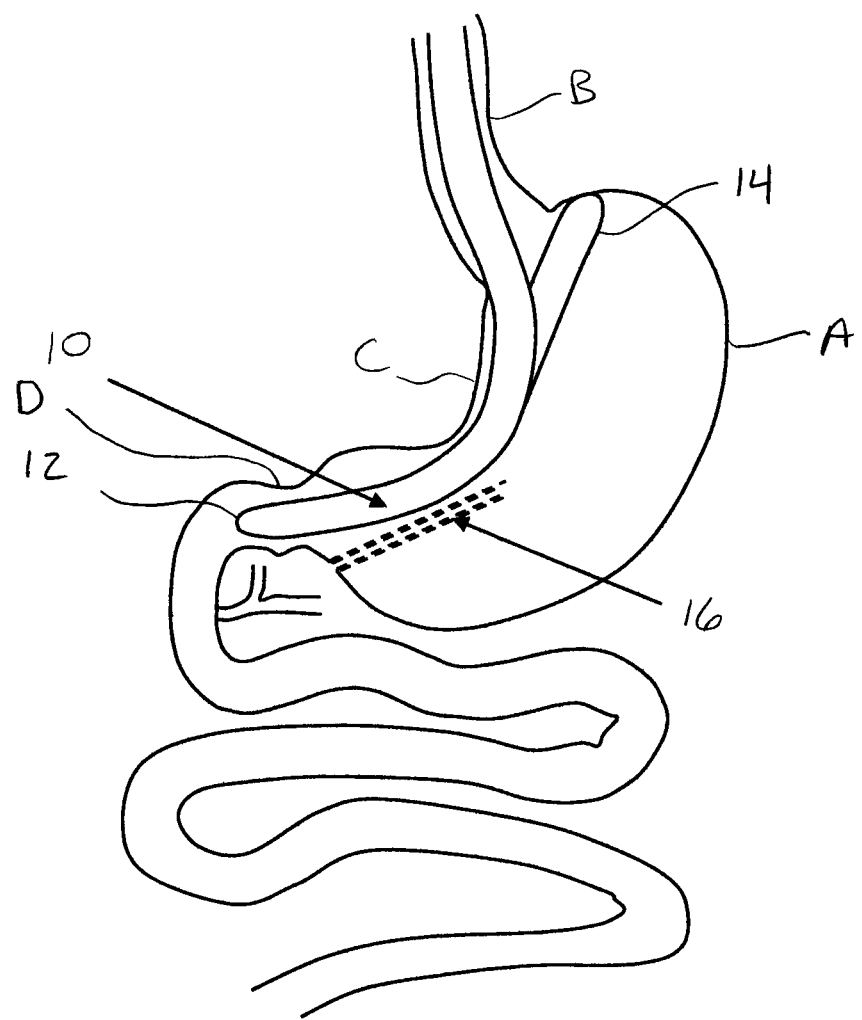
FIG. 3 is an elevation of a third step of the method of the present invention.
Figure 4:
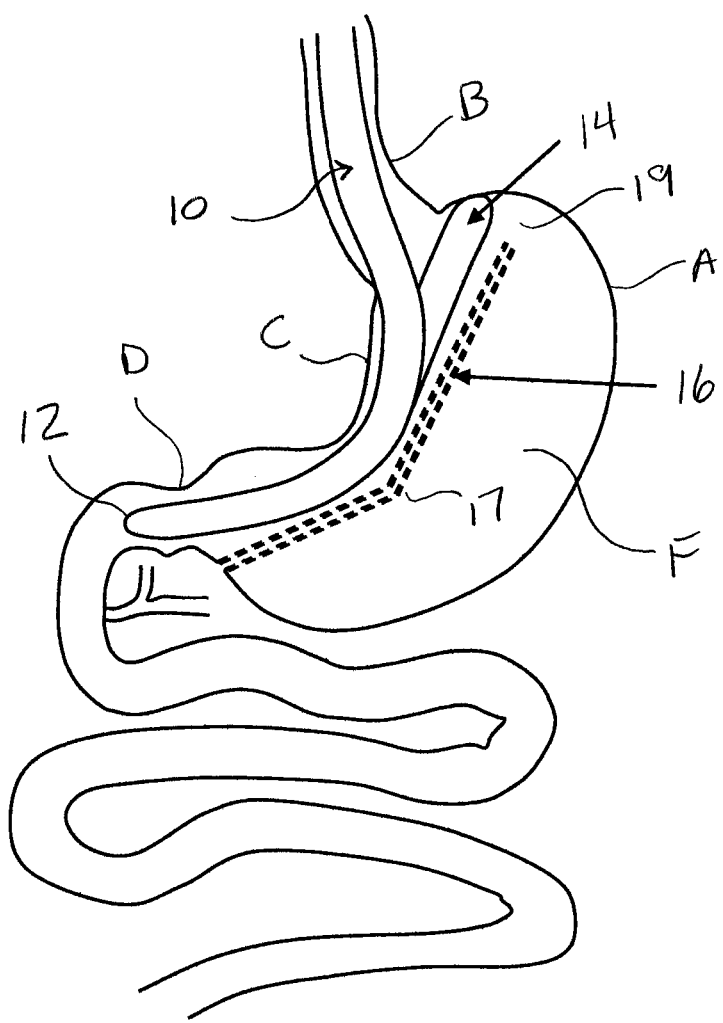
FIG. 4 is an elevation of a fourth step of the method of the present invention.

Next, as seen in FIG. 3, a staple line 16 is followed along the inner edge 15 of the bougie 10 beginning at the bottom of the stomach A and working up toward the esophagus B. Optionally, suction may be applied to the stomach A, such that the stomach A collapses and is sucked against the bougie 10, making the bougie 10 and the desired staple line 16 easier to visualize and follow. Additionally or alternatively, the bougie 10 may include a light source visible through the wall of the stomach A, thereby improving visibility. As seen in FIG. 4, the suture line 16 will likely include a bend 17 or angle that follows the bougie 10.

Figure 5:
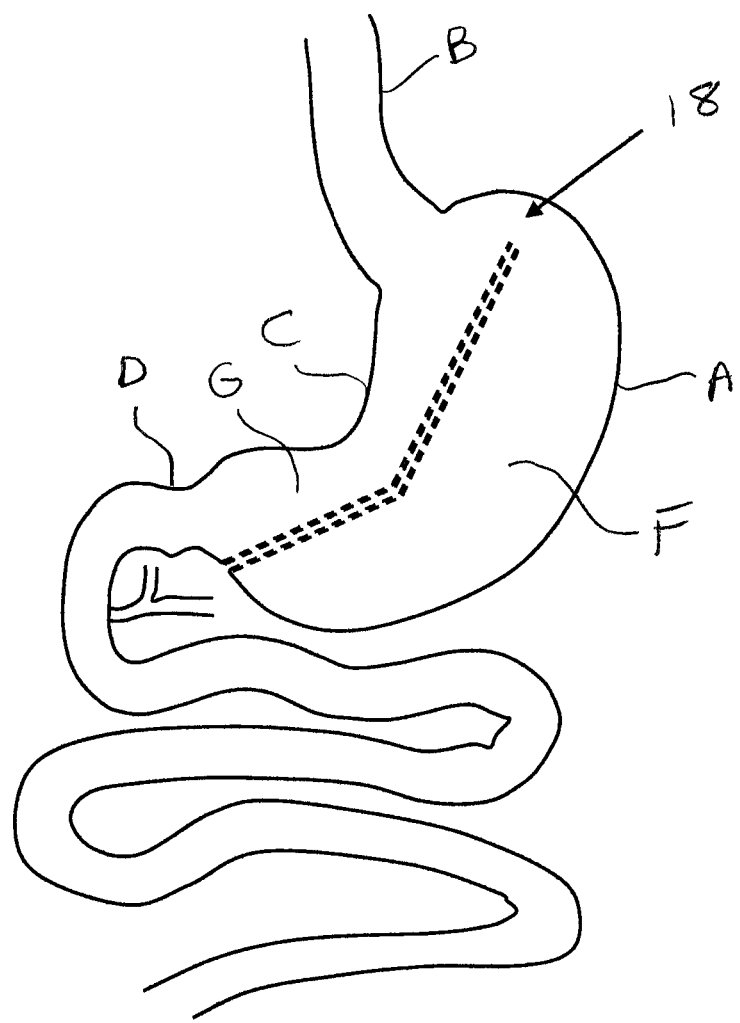
FIG. 5 is an elevation of stomach having undergone the method of the present invention.

FIG. 5 shows that the suture line 16 ends prior to reaching the top of the stomach. A space 19 is left that allows some communication between the bypassed portion of the stomach F and the newly formed stoma G. After the staple line 16 is complete, the extension 14 is closed against the bougie 10 and the bougie 10 is retracted through the esophagus B.

Turning now to FIGS. 6-7, there are shown several embodiments of bougies suitable for use with the method of the present invention.

FIG. 6 shows a bougie 20 with an extension 22 and an activation device 24. The extension 22 is biased shut but is flexible enough to be held open using the activation device 24.

The activation device 24 includes a sliding ring 26 that passes around the outside of the bougie 20 but not including the extension 22. An extending wire 28 passes through an internal lumen of the bougie 20 and exits the bougie through a port 30 located distally of a distal end 32 of the extension 22. The extending wire 28 is then routed proximally and attached to the sliding ring 26. Preferably, though not shown in the figures, a second extending wire is similarly routed on an opposite side of the bougie 20 such that when pulled, and equal force is applied to both sides of the ring 26, thereby preventing the ring from hanging up on the bougie 20.

One or preferably two (one shown) retraction wires 34 are also routed through an internal lumen of the bougie, exiting at a port 36 located proximally of the proximal end 38 of the bougie 20. The retraction wires 34 are also connected to the sliding ring 26.

In operation, the bougie 20 is placed as desired in the stomach and the extension 22 is splayed open by pulling on the extending wire or wires 28, thereby pulling the ring 26 down in a distal direction. The ring 26 is wedged between the extension 22 and the rest of the bougie 20. The further the ring 26 is pulled toward the junction between the extension 22 and the bougie 20, the greater the angle between the two becomes.

When the extension 22 is splayed a desired amount, the stapling step of the procedure is accomplished. To remove the bougie 20, the retraction wire or wires 34 are pulled, thereby pulling the sliding ring 26 in a proximal direction. The resilient nature of the extension 22 brings it flush against the bougie 20 and the bougie 20 may be removed.

Turning now to FIG. 7, there is shown another embodiment of a bougie 40 of the present invention with an extension 42 and an activation device 44. The extension 42 is biased open but is flexible enough to be held closed using the activation device 44.

The activation device 44 includes a sliding ring 46 that passes around the outside of the bougie 40, including the extension 42. An extending wire 48 passes through an internal lumen of the bougie 40 and exits the bougie through a port 50 located near or distally of a distal end 52 of the extension 42. The extending wire 48 is then routed proximally and attached to the sliding ring 46. Preferably, though not shown in the figures, a second extending wire is similarly routed on an opposite side of the bougie 40 such that when pulled, and equal force is applied to both sides of the ring 46, thereby preventing the ring from hanging up on the bougie 40.

One or preferably two (one shown) retraction wires 54 are also routed through an internal lumen of the bougie, exiting at a port 56 located proximally of the proximal end 58 of the bougie 40. The retraction wires 54 are also connected to the sliding ring 46.

In operation, the bougie 40 is placed as desired in the stomach and the extension 42 is splayed open by pulling on the extending wire or wires 48, thereby pulling the ring 26 down in a distal direction. The ring 46 releases the extension 42 and the biased-open extension is free to splay. Depending on the how over-sized the ring 46 is compared to the bougie, the further the ring 46 is pulled toward the junction between the extension 42 and the bougie 40, the greater the angle between the two becomes.

When the extension 42 is splayed a desired amount, the stapling step of the procedure is accomplished. To remove the bougie 40, the retraction wire or wires 54 are pulled, thereby pulling the sliding ring 46 in a proximal direction. The ring 46 collapses the extension 42 flush against the bougie 40 and the bougie 40 may be removed. Preferably the port 56 is located such that the ring 46 cannot be drawn past the proximal end of the extension 42, such that an accidental splaying of the extension 42 during withdrawal is not possible.

Although the invention has been described in terms of particular embodiments and applications, one of ordinary skill in the art, in light of this teaching, can generate additional embodiments and modifications without departing from the spirit of or exceeding the scope of the claimed invention. For example, one skilled in the art will realize several embodiments bougies that include an extension and various was to deploy and retract this extension. Just a few, non-limiting examples of other devices include, but are not limited to, screw-activated devices, balloon activated devices, ratcheting devices, and the like. Accordingly, it is to be understood that the drawings and descriptions herein are proffered by way of example to facilitate comprehension of the invention and should not be construed to limit the scope thereof.

We claim:

1. A method of performing a gastroplasty without resection comprising:
    passing a bougie into a stomach of a patient, said bougie including a body having portion configured to enter the stomach, said portion having a distal end and a proximal end and an extension capable of splaying away from said proximal end to form a Y shape;
    splaying said extension;
    joining opposing walls of the stomach along an outer side of said extension that is opposite said body;
    closing said extension against said body;
    removing said bougie.

2. The method of claim 1 wherein joining opposing wall of the stomach along an outer side of said extension that is opposite said body comprises: establishing a line along an outer side of said extension, beginning at a bottom of the stomach and ending at a point that is spaced below and away from a gastroesophageal junction due to said splaying of said extension.

3. The method of claim 2 wherein joining opposing walls of the stomach along an outer side of said extension that is opposite said body comprises joining opposing walls of the stomach along said line.

4. The method of claim 1 further comprising applying suction to said stomach, thereby causing said opposing walls to collapse around said bougie.

5. The method of claim 1 further comprising activating a light source on said bougie.

6. The method of claim 1 wherein splaying said extension comprises activating a splaying mechanism.

7. The method of claim 6 wherein said splaying mechanism urges said extension away from said body.

8. The method of claim 6 wherein said splaying mechanism allows said extension to spring away from said body.

9. The method of claim 1 wherein said splaying mechanism comprises:
    an activation mechanism that allows a user to splay said extension away from said body and to return said extension back to a collapsed state wherein said extension is not splayed away from said body.

10. The method of claim 1 wherein said portion is curved to follow a lesser curve of the stomach.

11. The method of claim 1 wherein said extension is biased to said collapsed state and said activation mechanism urges said extension to a splayed state.

12. The method of claim 1 wherein said extension is biased to a splayed state and said activation mechanism urges said extension to said collapsed state.

* * * * *